United States Patent
Nagamatsu et al.

(10) Patent No.: US 10,272,021 B2
(45) Date of Patent: Apr. 30, 2019

(54) COMPOSITION BASED ON MULTILAYER SPHERICAL COMPOSITE PARTICLES AND ON A UV-SCREENING AGENT

(71) Applicant: L'OREAL, Paris (FR)

(72) Inventors: Yasuko Nagamatsu, Kanagawa (JP); Didier Candau, Bievres (FR); Angelina Roudot, Le Kremlin Bicêtre (FR); Yannick Jolly, Epinay S/s Senart (FR)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 15/513,018

(22) PCT Filed: Sep. 16, 2015

(86) PCT No.: PCT/EP2015/071218
§ 371 (c)(1),
(2) Date: Mar. 21, 2017

(87) PCT Pub. No.: WO2016/042027
PCT Pub. Date: Mar. 24, 2016

(65) Prior Publication Data
US 2017/0304160 A1 Oct. 26, 2017

(30) Foreign Application Priority Data
Sep. 19, 2014 (FR) .................................. 14 58871

(51) Int. Cl.
| | | |
|---|---|---|
| *A61K 8/02* | (2006.01) |
| *A61K 8/25* | (2006.01) |
| *A61K 8/29* | (2006.01) |
| *A61Q 17/04* | (2006.01) |
| *A61K 8/34* | (2006.01) |
| *A61K 8/35* | (2006.01) |
| *A61K 8/37* | (2006.01) |
| *A61K 8/40* | (2006.01) |
| *A61K 8/41* | (2006.01) |
| *A61K 8/44* | (2006.01) |
| *A61K 8/46* | (2006.01) |
| *A61K 8/49* | (2006.01) |
| *A61K 8/58* | (2006.01) |
| *A61K 8/67* | (2006.01) |
| *A61K 8/81* | (2006.01) |
| *A61K 8/84* | (2006.01) |
| *A61K 8/86* | (2006.01) |
| *A61Q 19/08* | (2006.01) |

(52) U.S. Cl.
CPC .............. *A61K 8/0266* (2013.01); *A61K 8/25* (2013.01); *A61K 8/29* (2013.01); *A61K 8/342* (2013.01); *A61K 8/345* (2013.01); *A61K 8/35* (2013.01); *A61K 8/37* (2013.01); *A61K 8/375* (2013.01); *A61K 8/40* (2013.01); *A61K 8/41* (2013.01); *A61K 8/44* (2013.01); *A61K 8/466* (2013.01); *A61K 8/4966* (2013.01); *A61K 8/585* (2013.01); *A61K 8/678* (2013.01); *A61K 8/8147* (2013.01); *A61K 8/8152* (2013.01); *A61K 8/84* (2013.01); *A61K 8/86* (2013.01); *A61Q 17/04* (2013.01); *A61Q 19/08* (2013.01); *A61K 2800/26* (2013.01); *A61K 2800/651* (2013.01)

(58) Field of Classification Search
CPC .. A61K 8/0266; A61K 2800/26; A61Q 17/04; A61Q 19/08
See application file for complete search history.

(56) References Cited

U.S. PATENT DOCUMENTS

2002/0172697 A1* 11/2002 Nakade .................... A61K 8/29
424/401
2003/0035883 A1 2/2003 Nishikata et al.

FOREIGN PATENT DOCUMENTS

| WO | WO 2007 007283 A1 | 1/2007 |
| WO | WO 2012 095786 A2 | 7/2012 |
| WO | WO 2012 104161 A1 | 8/2012 |

\* cited by examiner

*Primary Examiner* — Carlos A Azpuru
(74) *Attorney, Agent, or Firm* — Polsinelli PC

(57) ABSTRACT

A subject matter of the present invention is a composition comprising:
a) at least multilayer spherical composite particles comprising
  i) a core comprising at least one material A having a refractive index ranging from 1.3 to 1.8; and
  ii) at least one layer covering said core, comprising at least one material B having a refractive index ranging from 1.9 to 3.1; and
  iii) optionally at least one second layer covering the material B, comprising at least one material C having a refractive index ranging from 1.3 to 1.8;
said composite particles being present in an amount less than 28.0% by weight relative to the total weight of the composition; and
b) at least one UV-screening agent.
This composition is for topical use and is more particularly intended for the photoprotection of the skin and/or hair against ultraviolet (UV) radiation.

17 Claims, No Drawings

COMPOSITION BASED ON MULTILAYER SPHERICAL COMPOSITE PARTICLES AND ON A UV-SCREENING AGENT

CROSS REFERENCE TO RELATED APPLICATIONS

This application is a National Phase filing under 35 U.S.C. § 371 of PCT/EP2015/071218 filed on Sep. 16, 2015; and this application claims priority to Application No. 1458871 filed in France on Sep. 19, 2014 under 35 U.S.C. § 119. The entire contents of each application are hereby incorporated by reference.

A subject of the present invention is a composition comprising:
a) at least multilayer spherical composite particles comprising
   i) a core comprising at least one material A having a refractive index ranging from 1.3 to 1.8; and
   ii) at least one layer covering said core, comprising at least one material B having a refractive index ranging from 1.9 to 3.1; and
   iii) optionally at least one second layer covering the material B, comprising at least one material C having a refractive index ranging from 1.3 to 1.8; and
said composite particles being present in an amount less than 28.0% by weight relative to the total weight of the composition; and
b) at least one UV-screening agent.

This composition is for topical use and is more particularly intended for the photoprotection of the skin and/or the hair against ultraviolet (UV) radiation.

It is known that radiation with wavelengths of between 280 nm and 400 nm permits tanning of the human epidermis and that radiation with wavelengths of between 280 and 320 nm, known as UVB rays, harm the development of a natural tan. Exposure is also liable to induce impairment in the biomechanical properties of the epidermis, which is reflected by the appearance of wrinkles, leading to premature ageing of the skin.

For these reasons, and also for aesthetic reasons, there is constant demand for means for controlling this natural tanning in order thus to control the colour of the skin; UVB radiation should thus be screened out.

It is also known that UVA rays with wavelengths of between 320 and 400 nm penetrate more deeply into the skin than UVB rays. UVA rays bring about immediate and persistent tanning of the skin. Daily exposure to UVA rays, even of short duration, under normal conditions can result in damage to the collagen fibres and the elastin, which is reflected by a modification to the microrelief of the skin, the appearance of wrinkles and uneven pigmentation (liver spots, non-uniformity of the complexion).

Protection against UVA and UVB radiation is therefore necessary. An effective photoprotective product must protect against both UVA and UVB radiation.

Many cosmetic compositions intended to limit darkening of the skin, and to improve the colour and uniformity of the complexion have been proposed to date. It is well known in the field of suntan products that such compositions can be obtained by using UV-screening agents, and in particular UVB-screening agents. Some compositions may also contain UVA-screening agents. This screening system must cover UVB protection for the purpose of limiting and controlling the neo-synthesis of melanin promoting overall pigmentation, but must also cover UVA protection in order to limit and control the oxidation of the already existing melanin resulting in darkening of the colour of the skin.

However, it is extremely difficult to find a composition containing a particular combination of UV-screening agents that would be specially suitable for photoprotection of the skin and particularly for an improvement in the quality of the skin both in terms of the colour and in terms of its mechanical elasticity properties.

Advantageously, this improvement is particularly desired on skin that is already pigmented, for the purpose of not increasing either the pigmentary melanin load or the structure of the melanin already present within the skin.

Many photoprotective compositions have been proposed to date to overcome the effects induced by UVA and/or UVB radiation. They generally contain organic UV-screening agents and/or inorganic UV-screening agents, which function according to their own chemical nature and according to their own properties by absorption, reflection or scattering of the UV radiation. They generally contain mixtures of liposoluble organic screening agents and/or of water-soluble UV-screening agents combined with metal oxide pigments such as titanium dioxide or zinc oxide.

Suntan compositions based on a UV-screening agent in free form and on spherical composite particles with an average size of between 0.1 µm and 30 µm comprising a matrix and an inorganic UV-screening agent are known in patent application WO 2012/104161. According to said document, these spherical particles are also combined with platelet-shaped composite particles with an average size of between 0.1 µm and 30 µm comprising a matrix and an inorganic UV-screening agent, such as the ultrafine particles of $TiO_2$ deposited on the surface of talc platelets having the trade name TTC 30® sold by the company Myoshi Kase. The applicant, during its research studies, has observed that, in the absence of the platelet-shaped composites, these compositions have neither sufficient stability nor entirely satisfactory cosmetic properties, such as a non-greasy feel, good spreading and good glide.

There remains therefore a need to provide novel sun protection compositions containing at least composite particles and at least one UV-screening agent in free form, which are effective in photoprotection, which have good stability and also good cosmetic properties such as easy spreading, a non-greasy feel and good glide, and which do not have the drawbacks presented above.

Unexpectedly and advantageously, the applicant has discovered that this need can be met by means of the compositions according to the present invention.

A first subject of the present invention relates to a composition comprising:
a) at least multilayer spherical composite particles comprising
   i) a core comprising at least one material A having a refractive index ranging from 1.3 to 1.8; and
   ii) at least one layer covering said core, comprising at least one material B having a refractive index ranging from 1.9 to 3.1; and
   iii) optionally at least one second layer covering the material B, comprising at least one material C having a refractive index ranging from 1.3 to 1.8;
said composite particles being present in an amount less than 28.0% by weight relative to the total weight of the composition; and
b) at least one UV-screening agent.

The composition according to the present invention is effective in photoprotection. Moreover, the composition has a homogeneous appearance, in particular on the microscopic scale and it does not generate a white deposit when it is applied to the skin. According to one particular form of the invention, the composition comprises a physiologically acceptable medium.

Another subject of the present invention consists of a cosmetic process for caring for and/or making up a keratin material, comprising the application, to the surface of said keratin material, of a composition according to the invention as defined above.

The invention also relates to a cosmetic process for limiting the darkening of the skin and/or improving the colour and/or uniformity of the complexion, comprising the application, to the surface of the keratin material, of a composition as defined previously.

It also relates to a cosmetic process for preventing and/or treating the signs of ageing of a keratin material, comprising the application, to the surface of the keratin material, of a composition as defined previously.

The description and the examples which follow present other advantages, aspects and properties of the present invention.

Definitions

The following definitions are used in the present text.

The term "human keratin materials" is intended to mean the skin (body, face, area around the eyes), hair, lips, mucous membranes.

The term "physiologically acceptable" is intended to mean compatible with the skin and/or appendages thereof, which has a pleasant colour, odour and feel and which does not generate unacceptable discomfort (tingling, tautness, redness), which may dissuade consumers from using this composition.

The term "preventing" or "prevention" is intended to mean, according to the invention, reducing the risk of occurrence or slowing down the occurrence of a given phenomenon, namely, according to the present invention, the signs of ageing of a keratin material.

The term "average size" of particles is intended to mean the diameter of the particles, measured by image analysis of electron microscopy images, for example scanning electron microscopy images.

The term "refractive index", often denoted n, is intended to mean the dimensionless magnitude characteristic of a material, describing the behaviour of light in said material.

The refractive index n, of a transparent medium, is defined by the ratio between the speed of propagation of light in a vacuum, c and its speed in this medium $v_1$.

$$n = c/v_1$$

In practice, the refractive index of a substance is measured with respect to air. The refractive index n depends on the wavelength λ of the incident light, and on the temperature at which the measurement is carried out. In an absorbent medium, the refractive index is a complex number, the imaginary part of which gives an account of the attenuation of the wave.

The refractive index in particular intervenes in the Snell-Descartes laws, which involve the ratio of the refractive indices.

Take a light ray passing through a surface separating two transparent media of respective indices ($n_1$) and ($n_2$). Take the angle i between the normal to the surface and the incident ray. The angle r of the refracted ray is obtained by:

$$n_1 \times \sin(i) = n_2 \times \sin(r)$$

The refractive indices according to the invention are measured at ambient temperature (20-25° C.) by means of a refractometer, most of the models of which take a measurement of the limiting angle of refraction. This method is described in "Cours de Physique Générale Optique" ["Courses in Optical General Physics" by G. Bruhat (pages I2 to I4, sixth edition, published by Masson).

The term "UV-screening agent" is intended to mean a molecule capable of screening out UV radiation between 290 and 400 nm.

The term "elementary average size" is intended to mean the size of non-aggregated particles.

The term "spherical" is intended to mean that the particle has a sphericity index, i.e. the ratio between its largest diameter and its smallest diameter is less than 1.2.

Composite Particles

The multilayer spherical composite particles in accordance with the invention comprise:
 i) a core comprising at least one material A having a refractive index ranging from 1.3 to 1.8;
 ii) at least one layer covering said core, comprising at least one material B having a refractive index ranging from 1.9 to 3.1;
 iii) optionally at least one second layer covering the material B, comprising at least one material C having a refractive index ranging from 1.3 to 1.8.

According to one particular form of the invention, the multilayer spherical composite particles comprise:
 i) a core comprising at least one material A having a refractive index ranging from 1.3 to 1.8;
 ii) at least one layer covering said core, comprising at least one material B having a refractive index ranging from 1.9 to 3.1; and
 iii) at least one second layer covering the material B, comprising at least one material C having a refractive index ranging from 1.3 to 1.8.

The various layers of the spherical composite particles according to the invention are generally concentric.

The spherical composite particles in accordance with the invention are preferably characterized by an average diameter ranging from 0.05 to 45 µm, more preferentially ranging from 0.05 to 10 µm and even more preferably ranging from 0.05 to 1 µm.

The spherical composite particles in accordance with the invention are present at concentrations less than 28.0% by weight relative to the total weight of the composition and preferably at concentrations ranging from 0.5% to 25% by weight relative to the total weight of the composition.

The materials A, B and C may consist of organic and/or inorganic substances.

The organic materials A and C having a refractive index of 1.3-1.8 may be chosen from the group formed by poly (meth)acrylates, polyamides, silicones, polyurethanes, polyethylenes, polypropylenes, polystyrenes, polycaprolactams, polysaccharides, polypeptides, polyvinyl derivatives, waxes, polyesters and polyethers, and mixtures thereof.

The inorganic materials A and C having a refractive index of 1.3-1.8 may be chosen from the group formed by glass, silica, calcium carbonate and aluminium oxide, and mixtures thereof.

Silica will more particularly be used for the materials A and C.

The inorganic material B having a refractive index of 1.9-3.1 may be chosen from metal oxides.

The metal oxides are preferably chosen from titanium, zinc, iron and zirconium oxides, or mixtures thereof, and more particularly from titanium dioxide and zinc oxide, and mixtures thereof.

Particularly preferably, titanium dioxide ($TiO_2$) will be used. In particular, the titanium dioxide ($TiO_2$) may be in rutile and/or anatase form and/or in an amorphous form.

These metal oxides may be in the form of particles with an average elementary size generally between 0.01 and 0.20 µm. Advantageously, the metal oxide particles used have an average size of less than 0.10 µm, even better still between 0.01 and 0.1 µm, and more particularly between 0.015 and 0.05 µm.

According to one particular form of the invention, the multilayer spherical composite particles in accordance with the invention comprise:
i) a core consisting of silica and
ii) at least one layer consisting of titanium dioxide covering said core and
iii) at least one second layer consisting of silica covering said titanium dioxide layer.

Preferentially, the core based on the material A represents from 1% to 99% by weight and more preferentially from 10% to 95% by weight relative to the total weight of the spherical composite particle.

Preferentially, the layer based on the material B represents from 0.5% to 50% by weight and more preferentially from 1% to 40% by weight relative to the total weight of the spherical composite particle.

Preferentially, the layer based on the material C represents from 0.5% to 50% by weight and more preferentially from 1% to 40% by weight relative to the total weight of the spherical composite particle.

Among the composite particles that can be used according to the invention, use will more particularly be made of the multilayer spherical composite particles with an average diameter of 0.6 µm consisting of 82% by weight of a silica core, 5% by weight of a first layer of titanium dioxide and 13% by weight of a second layer of silica, such as the product sold under the trade name STM ACS-0050510, supplied by the company JGC Catalysts and Chemical.

The composite particles in accordance with the invention are known as such. The definitions thereof and the method for preparing same are described in patent JP 360 5118.

They can be obtained according to a preparation process comprising the following steps. In a first step, hydrolysis of an alkoxysilane in ethanolic solution (i.e. Monomethyltriethoxysilane) is carried out, with stirring, in the presence of aqueous ammonia, followed by calcination in order to obtain spherical silica particles. A metal hydrolysate (i.e. titanium hydrolysate) is prepared with an alcoholic solution of metal oxide alkoxide (i.e. solution of a titanium isopropoxide in isopropanol), with stirring in a nitrogenous medium, and then, after filtration and rinsing, the resulting powder is heated at 300° C. for 4 hours and left to cool to ambient temperature. The resulting hydrolysate is made to adhere to the surface of the spherical silica particles in the presence of alcohol in order to obtain the first layer of metal oxide internal coating of the composite particles. Filtration and rinsing are carried out and the resulting powder is heated at 300° C. for 4 hours and left to cool to ambient temperature. The powder thus coated is then brought into contact with an ethanolic solution of alkoxysilane (i.e. Tetraethoxysilane) in the presence of hydrochloric acid, with stirring, for 24 hours. A second external layer of silica is thus formed and then optionally subsequently calcined.

a) UV-Screening Agents

The compositions according to the invention comprise one or more UV-screening agents chosen from water-soluble, liposoluble or insoluble organic UV-screening agents, and/or one or more inorganic UV-screening agents.

According to one particular form of the invention, the UV-screening agent(s) used is (are) in free form.

The term "UV-screening agent in free form" is intended to mean a molecule which is capable of screening out UV radiation between 280 and 400 nm and which is not bonded to a matrix in composite particles.

The term "water-soluble organic UV-screening agent" is intended to mean any organic compound for screening out UV radiation, which can be fully dissolved in molecular form or made miscible in an aqueous phase or else can be dissolved in colloidal form (for example in micellar form) in an aqueous phase.

The term "liposoluble organic UV-screening agent" is intended to mean any organic compound for screening out UV radiation, which can be fully dissolved in molecular form or made miscible in an oily phase or else can be dissolved in colloidal form (for example in micellar form) in an oily phase.

The term "insoluble organic UV-screening agent" is intended to mean any organic compound for screening out UV radiation which has a solubility in water of less than 0.5% by weight and a solubility of less than 0.5% by weight in the majority of organic solvents such as liquid paraffin, fatty alcohol benzoates and fatty acid triglycerides, for example Miglyol 812® sold by the company Dynamit Nobel. This solubility, determined at 70° C., is defined as the amount of product in solution in the solvent at equilibrium with an excess of solid in suspension after returning to ambient temperature. It may be readily evaluated in the laboratory.

The organic UV-screening agents are chosen in particular from cinnamic compounds; anthranilate compounds; salicylic compounds; dibenzoylmethane compounds; benzylidenecamphor compounds; benzophenone compounds; β,β-diphenylacrylate compounds; triazine compounds; benzotriazole compounds; benzalmalonate compounds, in particular those cited in U.S. Pat. No. 5,624,663; benzimidazole compounds; imidazoline compounds; bis-benzazolyl compounds, as described in patents EP 669 323 and U.S. Pat. No. 2,463,264; p-aminobenzoic (PABA) compounds; methylenebis(hydroxyphenylbenzotriazole) compounds, as described in applications U.S. Pat. No. 5,237,071, U.S. Pat. No. 5,166,355, GB 2 303 549, DE 197 26 184 and EP 893 119; benzoxazole compounds, as described in patent applications EP 0 832 642, EP 1 027 883, EP 1 300 137 and DE 101 62 844; screening polymers and screening silicones, such as those described in particular in application WO 93/04665; α-alkylstyrene-based dimers, such as those described in patent application DE 198 55 649; 4,4-diarylbutadiene compounds, as described in applications EP 0 967 200, DE 197 46 654, DE 197 55 649, EP-A-1 008 586, EP 1 133 980 and EP 133 981; merocyanines as described in patent U.S. Pat. No. 4,195,999, application WO 2004/006878, applications WO 2008/090066, WO 2011/113718 and WO 2009/027258, and the documents IP COM Journal No. 000179675D published on 23 Feb. 2009, IP COM Journal No. 000182396D published on 29 Apr. 2009, IP COM Journal No. 000189542D published on 12 Nov. 2009 and IP COM Journal No. IPCOM000011179D published on 4 Mar. 2004, and mixtures thereof.

As examples of organic photoprotective agents, mention may be made of those denoted hereinbelow under their INCI name:

Cinnamic Compounds:
Ethylhexyl methoxycinnamate sold in particular under the trade name Parsol MCX® by DSM Nutritional Products,
Isopropyl methoxycinnamate,
Isoamyl p-methoxycinnamate sold under the trade name Neo Heliopan E 1000® by Symrise,
DEA methoxycinnamate,
Diisopropyl methylcinnamate,
Glyceryl ethylhexanoate dimethoxycinnamate.
Dibenzoylmethane Compounds:
Butylmethoxydibenzoylmethane, sold in particular under the trade name Parsol 1789® by DSM Nutritional Products,
Isopropyldibenzoylmethane.
Para-Aminobenzoic Compounds:
PABA,
Ethyl PABA,
Ethyl dihydroxypropyl PABA,
Ethylhexyl dimethyl PABA, sold in particular under the name Escalol 507® by ISP,
Glyceryl PABA,
PEG-25 PABA, sold under the name Uvinul P 25® by BASF.
Salicylic Compounds:
Homosalate, sold under the name Eusolex HMS® by Rona/EM Industries, Ethylhexyl salicylate, sold under the name Neo Heliopan OS® by Symrise, Dipropylene glycol salicylate, sold under the name Dipsal® by Scher, TEA salicylate, sold under the name Neo Heliopan TS® by Symrise.
β,β-Diphenylacrylate Compounds:
Octocrylene, sold in particular under the trade name Uvinul N 539® by BASF, Etocrylene, sold in particular under the trade name Uvinul N 35® by BASF.
Benzophenone Compounds:
Benzophenone-1, sold under the trade name Uvinul 400® by BASF,
Benzophenone-2, sold under the trade name Uvinul D 50® by BASF,
Benzophenone-3 or Oxybenzone, sold under the trade name Uvinul M 40® by BASF,
Benzophenone-4, sold under the trade name Uvinul MS 40® by BASF, Benzophenone-5,
Benzophenone-6 sold under the trade name Helisorb 11® by Norquay,
Benzophenone-8 sold under the trade name Spectra-Sorb UV-24® by American Cyanamid,
Benzophenone-9, sold under the trade name Uvinul DS 49® by BASF, Benzophenone-12,
n-Hexyl 2-(4-diethylamino-2-hydroxybenzoyl)benzoate, sold under the trade name Uvinul A Plus® or, as a mixture with octyl methoxycinnamate, under the trade name Uvinul A Plus B® by the company BASF,
1,1'-(1,4-Piperazinediyl)bis[1-[2-[4-(diethylamino)-2-hydroxybenzoyl]phenyl]methanone] (CAS 919803-06-8), as described in patent application WO 2007/071 584; this compound advantageously being used in micronized form (average size of 0.02 to 2 μm), which may be obtained, for example, according to the micronization process described in patent applications GB-A-2 303 549 and EP-A-893 119, and in particular in the form of an aqueous dispersion.
Benzylidenecamphor Compounds:
3-Benzylidenecamphor, manufactured under the name Mexoryl SD® by Chimex,
4-Methylbenzylidenecamphor, sold under the name Eusolex 6300® by Merck,
Benzylidenecamphorsulfonic acid, manufactured under the name Mexoryl SL® by Chimex,
Camphor benzalkonium methosulfate, manufactured under the name Mexoryl SO® by Chimex,
Terephthalylidenedicamphorsulfonic acid, manufactured under the name Mexoryl SX® by Chimex,
Polyacrylamidomethylbenzylidenecamphor, manufactured under the name Mexoryl SW® by Chimex.
Phenylbenzimidazole Compounds:
Phenylbenzimidazolesulfonic acid, sold in particular under the trade name
Eusolex 232® by Merck.
Bis-Benzazolyl Compounds:
Disodium phenyl dibenzimidazole tetrasulfonate, sold under the trade name Neo Heliopan AP® by Symrise.
Phenylbenzotriazole Compounds:
Drometrizole trisiloxane, sold under the name Silatrizole® by Rhodia Chimie.
Methylenebis(Hydroxyphenylbenzotriazole) Compounds:
Methylenebis(benzotriazolyl)tetramethylbutylphenol, in particular in solid form, such as the product sold under the trade name Mixxim BB/100® by Fairmount Chemical, or in the form of an aqueous dispersion of micronized particles with an average particle size ranging from 0.01 to 5 μm, more preferentially from 0.01 to 2 μm and more particularly from 0.020 to 2 μm, with at least one alkylpolyglycoside surfactant having the structure $C_nH_{2n+1}O(C_6H_{10}O_5)_xH$, in which n is an integer from 8 to 16 and x is the mean degree of polymerization of the $(C_6H_{10}O_5)$ unit and ranges from 1.4 to 1.6, as described in patent GB-A-2 303 549, sold in particular under the trade name Tinosorb M® by the company BASF, or in the form of an aqueous dispersion of micronized particles with an average particle size ranging from 0.02 to 2 μm, more preferentially from 0.01 to 1.5 μm and more particularly from 0.02 to 1 μm, in the presence of at least one polyglyceryl mono($C_8$-$C_{20}$)alkyl ester with a degree of glycerol polymerization of at least 5, such as the aqueous dispersions described in patent application WO 2009/063 392.
Triazine Compounds:
  Bis(ethylhexyloxyphenol)methoxyphenyltriazine, sold under the trade name Tinosorb S® by BASF,
  Ethylhexyltriazone sold in particular under the trade name Uvinul T 150® by BASF,
  Diethylhexyl butamido triazone, sold under the trade name Uvasorb HEB® by Sigma 3V,
  2,4,6-tris(dineopentyl 4'-aminobenzalmalonate)-s-triazine,
  2,4,6-tris(diisobutyl 4'-aminobenzalmalonate)-s-triazine,
  2,4-bis(n-butyl 4'-aminobenzoate)-6-(aminopropyltrisiloxane)-s-triazine,
  2,4-bis(dineopentyl 4'-aminobenzalmalonate)-6-(n-butyl 4'-aminobenzoate)-s-triazine,
  symmetrical triazine screening agents substituted with naphthalenyl groups or polyphenyl groups described in patent U.S. Pat. No. 6,225,467, patent application WO 2004/085 412 (see compounds 6 and 9) or the document "Symmetrical Triazine Derivatives", IP.COM IPCOM000031257 Journal, INC West Henrietta, N.Y., US (20 Sep. 2004), in particular 2,4,6-tris(diphenyl)triazine and 2,4,6-tris(terphenyl)triazine, which is also mentioned in patent applications WO 06/035 000, WO 06/034 982, WO 06/034 991, WO 06/035 007, WO 2006/034 992 and WO 2006/034 985, these compounds advantageously being used in micronized form (mean particle size of 0.02 to 3 μm), which may be obtained, for example, according to the micronization process described in patent applications GB-A-2 303 549 and EP-A-893 119, and in particular in aqueous dispersion form, silicone triazines substituted with two aminobenzoate groups, as described in patent EP 0 841 341, in particular 2,4-bis(n-butyl 4'-aminobenzalmalonate)-6-[(3-{1,3,3,3-tetramethyl-1-[(trimethylsilyl)oxy] disiloxanyl}propyl)amino]-s-triazine.

Anthranilic Compounds:
Menthyl anthranilate, sold under the trade name Neo Heliopan MA® by Symrise.

Imidazoline Compounds:
Ethylhexyl dimethoxybenzylidene dioxoimidazoline propionate.

Benzalmalonate Compounds:
Polyorganosiloxane containing benzalmalonate functional groups, for instance Polysilicone-15, sold under the trade name Parsol SLX® by DSM Nutritional Products.

4,4-Diarylbutadiene Compounds:
1,1-dicarboxy(2,2'-dimethylpropyl)-4,4-diphenylbutadiene.

Benzoxazole Compounds:
2,4-bis[5-(1,1-dimethylpropyl)benzoxazol-2-yl(4-phenyl) imino]-6-(2-ethylhexyl)imino-1,3,5-triazine, sold under the name Uvasorb K2A® by Sigma 3V.

The preferential organic screening agents in free form are chosen from: Ethylhexyl methoxycinnamate,
Ethylhexyl salicylate,
Homosalate,
Butyl methoxy dibenzoylmethane,
Octocrylene,
Phenylbenzimidazolesulfonic acid,
Benzophenone-3,
Benzophenone-4,
Benzophenone-5,
n-Hexyl 2-(4-diethylamino-2-hydroxybenzoyl)benzoate,
4-Methylbenzylidenecamphor,
Terephthalylidenedicamphorsulfonic acid,
Disodium phenyl dibenzimidazole tetrasulfonate,
Methylenebis(benzotriazolyl)tetramethylbutylphenol,
Bis(ethylhexyloxyphenol)methoxyphenyltriazine,
Ethylhexyl triazone,
Diethylhexyl butamido triazone,
2,4,6-tris(dineopentyl 4'-aminobenzalmalonate)-s-triazine,
2,4,6-tris(diisobutyl 4'-aminobenzalmalonate)-s-triazine,
2,4-bis(n-butyl 4'-aminobenzoate)-6-(aminopropyltrisiloxane)-s-triazine,
2,4-bis(dineopentyl 4'-aminobenzalmalonate)-6-(n-butyl 4'-aminobenzoate)-s-triazine,
2,4,6-tris(diphenyl)triazine,
2,4,6-tris(terphenyl)triazine,
2,4-bis(n-butyl 4'-aminobenzalmalonate)-6-[(3-{1,3,3,3-tetramethyl-1-[(trimethylsilyl)oxy]disiloxanyl}propyl) amino]-s-triazine,
Drometrizole trisiloxane,
Polysilicone-15,
1,1-dicarboxy(2,2'-dimethylpropyl)-4,4-diphenylbutadiene,
2,4-bis[5-(1,1-dimethylpropyl)benzoxazol-2-yl(4-phenyl) imino]-6-(2-ethylhexyl)imino-1,3,5-triazine,
and mixtures thereof.

The particularly preferred organic screening agents in free form are chosen from:
Ethylhexyl methoxycinnamate,
Ethylhexyl salicylate,
Homosalate,
Butyl methoxy dibenzoylmethane,
Octocrylene,
Phenylbenzimidazolesulfonic acid,
n-Hexyl 2-(4-diethylamino-2-hydroxybenzoyl)benzoate,
Terephthalylidenedicamphorsulfonic acid,
Methylenebis(benzotriazolyl)tetramethylbutylphenol,
2,4,6-tris(diphenyl)triazine,
Bis(ethylhexyloxyphenol)methoxyphenyltriazine,
Ethylhexyl triazone,
Diethylhexyl butamido triazone,
Drometrizole trisiloxane,
and mixtures thereof.

The inorganic UV-screening agents used in accordance with the present invention are metal oxide pigments. More preferentially, the inorganic UV-screening agents of the invention are metal oxide particles with an average elementary particle size of less than or equal to 0.5 µm, more preferentially between 0.005 and 0.5 µm, even more preferentially between 0.01 and 0.2 µm, better still between 0.01 and 0.1 µm and more particularly between 0.015 and 0.05 µm.

They may be chosen in particular from titanium oxide, zinc oxide, iron oxide, zirconium oxide and cerium oxide, or mixtures thereof.

Such coated or uncoated metal oxide pigments are described in particular in patent application EP-A-0 518 773. Commercial pigments that may be mentioned include the products sold by the companies Sachtleben Pigments, Tayca, Merck and Degussa.

The metal oxide pigments may be coated or uncoated.

The coated pigments are pigments that have undergone one or more surface treatments of chemical, electronic, mechanochemical and/or mechanical nature with compounds such as amino acids, beeswax, fatty acids, fatty alcohols, anionic surfactants, lecithins, sodium, potassium, zinc, iron or aluminium salts of fatty acids, metal alkoxides (of titanium or aluminium), polyethylene, silicones, proteins (collagen, elastin), alkanolamines, silicon oxides, metal oxides or sodium hexametaphosphate.

The coated pigments are more particularly titanium oxides that have been coated:
with silica, such as the product Sunveil® from the company Ikeda,
with silica and iron oxide, such as the product Sunveil F® from the company Ikeda,
with silica and alumina, such as the products Microtitanium Dioxide MT 500 SA® and Microtitanium Dioxide MT 100 SA from the company Tayca and Tioveil from the company Tioxide,
with alumina, such as the products Tipaque TTO-55 (B)® and Tipaque TTO-55 (A)® from the company Ishihara and UVT 14/4 from the company Sachtleben Pigments,
with alumina and aluminium stearate, such as the products Microtitanium Dioxide MT 100 T®, MT 100 TX®, MT 100 Z®, MT-01® and MT700Z® from the company Tayca, the products Solaveil CT-10 W® and Solaveil CT 100® from the company Uniqema and the product Eusolex T-AVO® from the company Merck,
with silica, alumina and alginic acid, such as the product MT-100 AQ® from the company Tayca,
with alumina and aluminium laurate, such as the product Microtitanium Dioxide MT 100 S® from the company Tayca,
with iron oxide and iron stearate, such as the product Microtitanium Dioxide MT 100 F® from the company Tayca,
with zinc oxide and zinc stearate, such as the product BR 351® from the company Tayca, with silica and alumina and treated with a silicone, such as the products Microtitanium Dioxide MT 600 SAS®, Microtitanium Dioxide MT 500 SAS® or Microtitanium Dioxide MT 100 SAS® from the company Tayca, with silica, alumina and aluminium stearate and treated with a silicone, such as the product STT-30-DS® from the company Titan Kogyo, with silica and treated with a silicone, such as the product UV-Titan X 195® from the company Sachtleben Pigments, with alumina and treated with a silicone, such as the products Tipaque TTO-55 (S)® from the company Ishihara or UV Titan M 262® from the company Sachtleben Pigments, with triethanolamine, such as the product STT-65-S from the company Titan Kogyo, with stearic acid, such as the product Tipaque TTO-55 (C)® from the company Ishihara, with sodium hexametaphosphate, such as the product Microtitanium Dioxide MT 150 W® from the company Tayca, $TiO_2$ treated with octyltrimethylsilane, sold under the trade name T 805® by the company Degussa Silices, $TiO_2$ treated with a polydimethylsiloxane, sold under the trade name 70250 Cardre UF TiO2SI3® by the company Cardre, anatase/rutile $TiO_2$ treated with a polydimethylhydrogenosiloxane, sold under the trade name Microtitanium Dioxyde USP Grade Hydrophobic® by the company Color Techniques.

The uncoated titanium oxide pigments are sold, for example, by the company Tayca under the trade names Microtitanium Dioxide MT 500 B or Microtitanium Dioxide MT 600 B®, by the company Degussa under the name P 25, by the company Wackherr under the name Transparent titanium oxide PW®, by the company Miyoshi Kasei under the name UFTR®, by the company Tomen under the name ITS® and by the company Tioxide under the name Tioveil AQ®.

The uncoated zinc oxide pigments are for example:

those sold under the name Z-Cote by the company Sunsmart;

those sold under the name Nanox® by the company Elementis;

those sold under the name Nanogard WCD 2025® by the company Nanophase Technologies.

The coated zinc oxide pigments are for example:

those sold under the name Zinc Oxide CS-5® by the company Toshibi (ZnO coated with polymethylhydrogenosiloxane);

those sold under the name Nanogard Zinc Oxide FN® by the company Nanophase Technologies (as a 40% dispersion in Finsolv TN®, $C_{12}$-$C_{15}$ alkyl benzoate);

those sold under the name Daitopersion Zn-30® and Daitopersion Zn-50® by the company Daito (dispersions in cyclopolymethylsiloxane/oxyethylenated polydimethylsiloxane, containing 30% or 50% of zinc oxides coated with silica and polymethylhydrogenosiloxane);

those sold under the name NFD Ultrafine ZnO® by the company Daikin (ZnO coated with perfluoroalkyl phosphate and copolymer based on perfluoroalkylethyl as a dispersion in cyclopentasiloxane);

those sold under the name SPD-Z1® by the company Shin-Etsu (ZnO coated with silicone-grafted acrylic polymer, dispersed in cyclodimethylsiloxane);

those sold under the name Escalol Z100® by the company ISP (alumina-treated ZnO dispersed in the ethylhexyl methoxycinnamate/PVP-hexadecene copolymer/methicone mixture);

those sold under the name Fuji ZnO-SMS-10® by the company Fuji Pigment (ZnO coated with silica and polymethylsilsesquioxane);

those sold under the name Nanox Gel TN® by the company Elementis (ZnO dispersed at a concentration of 55% in $C_{12}$-$C_{15}$ alkyl benzoate with hydroxystearic acid polycondensate).

The uncoated cerium oxide pigments may be, for example, those sold under the name Colloidal Cerium Oxide® by the company Rhone-Poulenc.

The uncoated iron oxide pigments are sold, for example, by the company Arnaud under the names Nanogard WCD 2002® (FE 45B®), Nanogard Iron FE 45 BL AQ®, Nanogard FE 45R AQ® and Nanogard WCD 2006® (FE 45R®) or by the company Mitsubishi under the name TY-220®.

The coated iron oxide pigments are sold, for example, by the company Arnaud under the names Nanogard WCD 2008 (FE 45B FN)®, Nanogard WCD 2009® (FE 45B 556®), Nanogard FE 45 BL 345® and Nanogard FE 45 BL® or by the company BASF under the name Transparent Iron Oxide®.

Mention may also be made of mixtures of metal oxides, in particular of titanium dioxide and of cerium dioxide, including the equal-weight mixture of titanium dioxide and cerium dioxide coated with silica, sold by the company Ikeda under the name Sunveil A®, and also the mixture of titanium dioxide and zinc dioxide coated with alumina, silica and silicone, such as the product M 261® sold by the company Sachtleben Pigments, or coated with alumina, silica and glycerol, such as the product M 211® sold by the company Sachtleben Pigments.

According to the invention, coated or uncoated titanium oxide pigments are particularly preferred.

The UV-screening agents in free form according to the invention are preferably present in the compositions according to the invention in a content ranging from 0.1% to 45% by weight and in particular from 5% to 30% by weight relative to the total weight of the composition.

Oily Phase

The compositions in accordance with the invention may contain at least one oily phase.

For the purposes of the invention, the term "oily phase" is intended to mean a phase comprising at least one oil and all of the liposoluble and lipophilic ingredients and the fatty substances used for the formulation of the compositions of the invention.

The term "oil" is intended to mean any fatty substance that is in liquid form at ambient temperature (20-25° C.) and at atmospheric pressure (760 mmHg).

An oil that is suitable for use in the invention may be volatile or non-volatile.

An oil that is suitable for use in the invention may be chosen from hydrocarbon-based oils, silicone oils and fluoro oils, and mixtures thereof.

A hydrocarbon-based oil that is suitable for use in the invention may be an animal hydrocarbon-based oil, a plant hydrocarbon-based oil, a mineral hydrocarbon-based oil or a synthetic hydrocarbon-based oil.

An oil that is suitable for use in the invention may be advantageously chosen from mineral hydrocarbon-based oils, plant hydrocarbon-based oils, synthetic hydrocarbon-based oils and silicone oils, and mixtures thereof.

For the purposes of the present invention, the term "silicone oil" is intended to mean an oil comprising at least one silicon atom, and in particular at least one Si—O group.

The term "hydrocarbon-based oil" is intended to mean an oil containing mainly hydrogen and carbon atoms.

The term "fluoro oil" is intended to mean an oil comprising at least one fluorine atom.

A hydrocarbon-based oil that is suitable for use in the invention may also optionally comprise oxygen, nitrogen, sulfur and/or phosphorus atoms, for example in the form of hydroxyl, amine, amide, ester, ether or acid groups, and in particular in the form of hydroxyl, ester, ether or acid groups.

The oily phase generally comprises, in addition to the lipophilic UV-screening agent(s), at least one volatile or non-volatile hydrocarbon-based oil and/or one volatile and/or non-volatile silicone oil.

For the purposes of the invention, the term "volatile oil" is intended to mean an oil that is capable of evaporating on contact with the skin or the keratin fibre in less than one hour, at ambient temperature and atmospheric pressure. The volatile oil(s) of the invention are volatile cosmetic oils which are liquid at ambient temperature and which have a non-zero vapour pressure, at ambient temperature and atmospheric pressure, ranging in particular from 0.13 Pa to 40 000 Pa ($10^{-3}$ to 300 mmHg), in particular ranging from 1.3 Pa to 13 000 Pa (0.01 to 100 mmHg) and more particularly ranging from 1.3 Pa to 1300 Pa (0.01 to 10 mmHg).

The term "non-volatile oil" is intended to mean an oil that remains on the skin or the keratin fibre at ambient temperature and atmospheric pressure for at least several hours, and that in particular has a vapour pressure of less than $10^{-3}$ mmHg (0.13 Pa).

Among the non-volatile hydrocarbon-based oils that can be used according to the invention, mention may be made of glyceride triesters and in particular caprylic/capric acid triglycerides such as those sold by the company Stearineries Dubois or those sold under the names Miglyol 810®, 812® and 818® by the company Dynamit Nobel, fatty amides such as isopropyl N-lauroyl sarcosinate, such as the product sold under the trade name Eldew SL 205® from Ajinomoto, synthetic esters, and in particular isononyl isononanoate, diisopropyl sebacate, such as the product sold under the trade name Dub Dis by the company Stearineries Dubois, dicapryl carbonate, such as the product sold under the trade name Cetiol CC® by BASF, $C_{12}$-$C_{15}$ alkyl benzoate, such as the product sold under the trade name Finsolv TN® or Witconol TN® by the company Witco or Tegosoft TN® by the company Evonik Goldschmidt, 2-ethylphenylbenzoate, such as the commercial product sold under the name X-Tend 226® by the company ISP, and fatty alcohols, in particular octyldodecanol.

As volatile hydrocarbon-based oils that may be used according to the invention, mention may be made in particular of hydrocarbon-based oils having from 8 to 16 carbon atoms and in particular of branched $C_8$-$C_{16}$ alkanes, such as $C_8$-$C_{16}$ isoalkanes of petroleum origin (also known as isoparaffins), such as isododecane (also known as 2,2,4,4, 6-pentamethylheptane), isodecane or isohexadecane, the oils sold under the Isopar or Permethyl trade names, branched $C_8$-$C_{16}$ esters, isohexyl neopentanoate, and mixtures thereof.

Among the non-volatile silicone oils, mention may be made of non-volatile polydimethylsiloxanes (PDMSs), polydimethylsiloxanes comprising alkyl or alkoxy groups which are pendent and/or at the end of the silicone chain, which groups each contain from 2 to 24 carbon atoms, or phenyl silicones, such as phenyl trimethicones, phenyl dimethicones, phenyl(trimethylsiloxy)diphenylsiloxanes, diphenyl dimethicones, diphenyl(methyldiphenyl)trisiloxanes or (2-phenylethyl)trimethylsiloxysilicates.

Examples of volatile silicone oils that may be mentioned include volatile linear or cyclic silicone oils, in particular those with a viscosity 8 centistokes ($8 \times 10^{-6}$ m²/s) and in particular containing from 2 to 7 silicon atoms, these silicones optionally comprising alkyl or alkoxy groups containing from 1 to 10 carbon atoms. As volatile silicone oil that may be used in the invention, mention may be made in particular of octamethylcyclotetrasiloxane, decamethylcyclopentasiloxane, dodecamethylcyclohexasiloxane, heptamethylhexyltrisiloxane, heptamethyloctyltrisiloxane, hexamethyldisiloxane, octamethyltrisiloxane, decamethyltetrasiloxane and dodecamethylpentasiloxane, and mixtures thereof.

Among the volatile fluoro oils, mention may be made of nonafluoromethoxybutane, decafluoropentane, tetradecafluorohexane and dodecafluoropentane, and mixtures thereof.

According to one particular form of the invention, the overall oily phase, including all the lipophilic substances of the composition capable of being dissolved in this same phase, represents from 5% to 95% by weight and preferentially from 10% to 80% by weight, relative to the total weight of the composition.

Aqueous Phase

The compositions according to the invention may also comprise at least one aqueous phase.

The aqueous phase contains water and optionally other water-soluble or water-miscible organic solvents.

An aqueous phase that is suitable for use in the invention may comprise, for example, a water chosen from a natural spring water, such as water from La Roche-Posay, water from Vittel or waters from Vichy, or a floral water.

The water-soluble or water-miscible solvents that are suitable for use in the invention comprise short-chain monoalcohols, for example $C_1$-$C_4$ monoalcohols, such as ethanol or isopropanol; diols or polyols, such as ethylene glycol, 1,2-propylene glycol, 1,3-butylene glycol, hexylene glycol, diethylene glycol, dipropylene glycol, 2-ethoxyethanol, diethylene glycol monomethyl ether, triethylene glycol monomethyl ether, glycerol and sorbitol, and mixtures thereof.

According to a preferred embodiment, use may more particularly be made of ethanol, propylene glycol, glycerol, and mixtures thereof.

According to one particular form of the invention, the overall aqueous phase, including all the hydrophilic substances of the composition capable of being dissolved in this same phase, represents from 5% to 95% by weight and preferentially from 10% to 80% by weight, relative to the total weight of the composition.

Additives:

The aqueous compositions in accordance with the present invention may also comprise standard cosmetic adjuvants chosen especially from organic solvents, ionic or non-ionic, hydrophilic or lipophilic thickeners, softeners, humectants, opacifiers, stabilizers, emollients, silicones, antifoams, fragrances, preserving agents, anionic, cationic, non-ionic, zwitterionic or amphoteric surfactants, active agents, fillers, polymers, propellants, acidifying or basifying agents or any other ingredient usually used in cosmetics and/or dermatology.

Among the acidifying agents, examples that may be mentioned include inorganic or organic acids, for instance hydrochloric acid, orthophosphoric acid, sulfuric acid, carboxylic acids, for instance acetic acid, tartaric acid, citric acid and lactic acid, and sulfonic acids.

As hydrophilic thickeners, mention may, for example, be made of carboxyvinyl polymers such as crosslinked copolymers of methacrylic acid and of $C_1$-$C_4$ alkyl acrylate, for instance the crosslinked methacrylic acid/ethyl acrylate copolymer sold by the company Noveon under the trade name Carbopol Aqua SF1® (present in the examples).

According to one particular form of the invention, the compositions comprise, in addition, at least one crosslinked copolymer of methacrylic acid and of $C_1$-$C_4$ alkyl acrylate, for instance the crosslinked methacrylic acid/ethyl acrylate copolymer sold by the company Noveon under the trade name Carbopol Aqua SF1®.

The concentration of copolymer preferably ranges from 0.01% to 10% by weight of active material relative to the total weight of the composition and preferably from 0.01% to 5% by weight of active material relative to the total weight of the composition.

According to one particular form of the invention, the compositions comprise, in addition, at least one semi-crystalline polymer which is solid at ambient temperature and which has a melting point greater than or equal to 30° C., comprising a) a polymer backbone and b) at least one crystallizable organic side chain and/or one crystallizable organic block which is part of the backbone of said polymer, said polymer having a number-average molecular weight Mn greater than or equal to 1000. This polymer is in particular described in application EP 2 911 269.

For the purposes of the invention, the term "polymers" is intended to mean compounds comprising at least 2 repeating units, preferably at least 3 repeating units and more especially at least 10 repeating units.

For the purposes of the invention, the term "semi-crystalline polymer" is intended to mean polymers comprising a crystallizable portion, crystallizable pendant chain or crystallizable block in the backbone, and an amorphous portion in the backbone, and having a first-order reversible change of phase temperature, in particular melting point (solid-liquid transition). When the crystallizable portion is in the form of a crystallizable block of the polymer backbone, the amorphous portion of the polymer is in the form of an amorphous block; the semicrystalline polymer is, in this case, a block copolymer, for example of the diblock, triblock or multiblock type, comprising at least one crystallizable block and at least one amorphous block.

The term "block" is generally intended to mean at least 5 identical repeating units. The crystallizable block(s) is (are) then of different chemical nature from the amorphous block(s).

For the purposes of the invention, the expression "crystallizable chain or block" is intended to mean a chain or block which, if it were obtained alone, would change from the amorphous state to the crystalline state reversibly, depending on whether one is above or below the melting point. For the purposes of the invention, a chain is a group of atoms, which are pendant or lateral relative to the polymer backbone. A block is a group of atoms belonging to the backbone, this group constituting one of the repeating units of the polymer. Advantageously, the "pendent crystallizable chain" may be a chain containing at least 6 carbon atoms.

According to one more particular embodiment of the invention, the polymer is derived from a monomer containing a crystallizable chain chosen from saturated $C_{14}$ to $C_{22}$ alkyl (meth)acrylates and even more particularly poly (stearyl acrylate)s, such as the product Intelimer® IPA 13-1 from the company Landec, or poly(behenyl acrylate)s, such as the product Intelimer® IPA 16-1 from the same company. More particularly, the product Intelimer® IPA 13-1 from the company Landec, which is a polystearyl acrylate with a molecular weight of about 145 000 and a melting point of 49° C., will be chosen.

The amount of semi-crystalline polymer in the composition of the invention may vary to a large extent according to the desired purpose. The amount of semi-crystalline polymers may range, for example, from 0.1% to 50% by weight of active material, preferably from 0.5% to 20% by weight of active material and better still from 1% to 10% by weight of active material relative to the total weight of the composition.

According to one particular form of the invention, the compositions of the invention comprise, in addition, hollow latex particles having a particle size ranging from 150 to 380 nm, such as those described in patent U.S. Pat. No. 5,663,213 and application EP 1 092 421.

The term "latex" is intended to mean particles of polymer in the form of an aqueous dispersion generally stabilized by at least one emulsifier.

For a given particle size, the latex particles according to the invention should generally have a maximum hollow fraction. Preferably, the latex particles contain an empty fraction of from 0.1% to 50% and more preferentially from 5% to 50%. The empty fractions are determined by comparing the volume occupied by the latex particles after having been compacted from a dilute dispersion in a centrifuge with respect to the volume of non-empty particles in the same composition.

The hollow latex particles according to the invention can be obtained from particles comprising at least one polymer for the core and at least one polymer for the shell. The core polymer and the shell polymer can be obtained from a single polymerization step or by means of a sequence of polymerization steps.

The hollow latex particles according to the invention can be prepared by the conventional techniques of emulsion polymerization. Such processes are in particular described in patents U.S. Pat. No. 4,427,836; U.S. Pat. No. 4,469,825; U.S. Pat. No. 4,594,363; U.S. Pat. No. 4,677,003; U.S. Pat. No. 4,920,160 and U.S. Pat. No. 4,970,241 or by the conventional polymerization techniques described in the following applications and patents: EP 267 726; EP 331 421; U.S. Pat. No. 490,229; U.S. Pat. No. 5,157,084.

According to one particular embodiment of the invention, use will be made of hollow latex particles consisting of a copolymer of styrene and of (meth)acrylic acid or one of the ($C_1$-$C_{20}$) alkyl esters thereof under the INCI name: Styrene/Acrylates Copolymer, for instance the product sold under the trade name Sunspheres Powder by the company Rohm & Haas which is an aqueous dispersion at 86% of Styrene/Acrylates Copolymer in a mixture of 11% of PEG-8 Laurate, of 2.5% water and of 0.5% of sodium dodecyl benzenesulfonate.

The hollow latex particles in accordance with the invention are preferably present in the composition of the invention in amounts ranging from 0.1% to 20% by weight and more preferentially from 0.5% to 10% by weight relative to the total weight of the composition.

Among the basifying agents, examples that may be mentioned include aqueous ammonia, alkali metal carbonates, alkanolamines, such as mono-, di- and triethanolamines and derivatives thereof, sodium hydroxide or potassium hydroxide.

Preferably, the cosmetic composition comprises one or more basifying agents chosen from alkanolamines, in particular triethanolamine, and sodium hydroxide.

In the case of an aqueous composition, the pH of the composition in accordance with the invention is generally between 3 and 12 approximately, preferably between 5 and 11 approximately and even more particularly from 6 to 8.5.

Needless to say, those skilled in the art will take care to choose the abovementioned optional additional compound(s) and/or the amounts thereof so that the advantageous properties intrinsically attached to the compositions in accordance with the invention are not, or not substantially, detrimentally affected by the envisaged addition(s).

Galenical Forms

The compositions according to the invention may be prepared according to the techniques that are well known to those skilled in the art. They may in particular be in the form of a simple or complex emulsion (O/W, W/O, O/W/O or W/O/W), such as a cream, a milk or a cream gel.

They may also be in anhydrous form, for instance in the form of an oil. The term "anhydrous composition" is intended to mean a composition containing less than 1% by weight of water, or even less than 0.5% of water, and especially free of water, the water not being added during the preparation of the composition but corresponding to the residual water provided by the mixed ingredients. They may optionally be packaged in aerosol form and may be in the form of a mousse or a spray.

In the case of compositions in the form of oil-in-water or water-in-oil emulsions, the emulsification processes that may be used are of the paddle or impeller, rotor-stator and HPH type.

In order to obtain stable emulsions with a low content of polymer (oil/polymer ratio >25), it is possible to prepare the dispersion in concentrated phase and then to dilute the dispersion with the remainder of the aqueous phase.

It is also possible, by means of HPH (between 50 and 800 bar), to obtain stable dispersions with drop sizes that may be as low as 100 nm.

The emulsions generally contain at least one emulsifier chosen from amphoteric, anionic, cationic and non-ionic emulsifiers, used alone or as a mixture. The emulsifiers are appropriately chosen according to the emulsion to be obtained (W/O or O/W).

According to one particular form of the invention, use will be made, as emulsifier, of a surfactant of formula (I) below, such as those described in application WO96/14926:

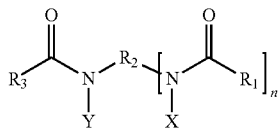
(I)

in which:
R$_1$ and R$_3$ denote, independently of each other, an alkyl radical containing from 1 to 25 carbon atoms;
R$_2$ denotes a spacer group consisting of a linear or branched alkylene chain containing from 1 to 12 carbon atoms;
X denotes a —(C$_2$H$_4$O)$_a$—(C$_3$H$_6$O)$_b$Z group
Y denotes a —(C$_2$H$_4$O)c-(C$_3$H$_6$O)$_d$Z group
where:
Z denotes a hydrogen atom or a —CH$_2$—COOM, —SO$_3$M, —P(O)(OM)$_2$, —C$_2$H$_4$—SO$_3$M, —C$_3$H$_6$—SO$_3$M or —CH$_2$ (CHOH)$_4$CH$_2$OH radical, where M, M' represent H or an alkali metal ion or alkaline-earth metal ion or ammonium ion or alkanolammonium ion,
a and c, independently of one another, range from 0 to 15,
b and d, independently of one another, range from 0 to 10, and
the sum of a+b+c+d ranges from 1 to 25; and
n ranges from 1 to 10.

R$_1$ and R$_3$ denote, independently of each other, preferably an alkyl radical containing from 5 to 21 and more particularly from 7 to 19 carbon atoms.

The surfactant of formula (I) is preferably such that each of the groups R$_1$—CO— and R$_3$—CO— comprises from 8 to 20 carbon atoms, and preferably denotes a coconut fatty acid residue (mainly comprising lauric acid and myristic acid).

Preferably, b and d are equal to 0.

In addition, this surfactant is preferably such that the sum of a, b, c and d has an average value ranging from 10 to 20 and is preferably from 12 to 18 and more particularly equal to 15.

A preferred group for Z is the group SO$_3$M, where M is preferably an alkali metal ion, such as a sodium ion.

The spacer group R$_2$ advantageously consists of a linear C$_1$-C$_3$ alkylene chain, and preferably an ethylene (—CH$_2$CH$_2$—) chain.

Finally, n is advantageously equal to 1.

A surfactant of this type is in particular the one identified by the INCI name: Disodium Ethylene Dicocamide PEG-15 Disulfate, having the following structure:

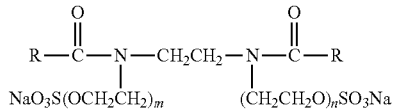

where RCO represents a coconut fatty acid radical and m+n has an average value of 15.

Preferably, the surfactant is used as a mixture with other surfactants, and in particular as a mixture with (a) an ester of a C$_6$-C$_{22}$ fatty acid (preferably C$_{14}$-C$_{20}$ such as a stearate) and of glyceryl, (b) a diester of a C$_6$-C$_{22}$ fatty acid (preferably C$_{14}$-C$_{20}$ such as a stearate) and of citric acid and glycerol (in particular a diester of a C$_6$-C$_{22}$ fatty acid and of glyceryl monocitrate), and (c) a C$_{10}$-C$_{30}$ fatty alcohol (preferably behenyl alcohol).

Advantageously, the composition according to the invention comprises a mixture of disodium ethylene dicocamide PEG-15 disulfate, of glyceryl stearate, of glyceryl stearate monocitrate and of behenyl alcohol.

More preferentially, the surfactant of formula (I) according to the invention represents from 10% to 20% by weight and advantageously 15% by weight; the glyceryl ester of a C$_6$-C$_{22}$ fatty acid represents from 30% to 40% by weight, advantageously 35% by weight; the diester of a C$_6$-C$_{22}$ fatty acid and of citric acid and of glycerol represents from 10% to 20% by weight, advantageously 15% by weight; and the C$_{10}$-C$_{30}$ fatty alcohol represents from 30% to 40% by weight, advantageously 35% by weight, relative to the total weight of the mixture of surfactants comprising the gemini surfactant.

Advantageously, the composition according to the invention comprises a mixture of from 10% to 20% by weight of disodium ethylene dicocamide PEG-15 sulfate, from 30% to 40% (in particular 35%) by weight of glyceryl stearate, from 10% to 20% (in particular 15%) by weight of glyceryl stearate monocitrate, and from 30% to 40% (in particular 35%) by weight of behenyl alcohol, relative to the total weight of the mixture of surfactants containing the gemini surfactant.

As a variant, the gemini surfactant according to the invention may be used as a mixture with an anionic surfactant, such as an ester of lauric acid, sodium lauroyl lactate. In this case, the gemini surfactant preferably represents from 30% to 50% by weight and the anionic surfactant represents from 50% to 70% by weight, relative to the total weight of the mixture.

The gemini surfactant may be used, for example, as a mixture with other surfactants in the form of the products sold by the company Sasol under the name Ceralution®, and in particular the following products:
  Ceralution® H: Behenyl Alcohol, Glyceryl Stearate, Glyceryl Stearate Citrate and disodium ethylene dicocamide PEG-15 disulfate,
  Ceralution® F: Sodium Lauroyl Lactylate et disodium ethylene dicocamide PEG-15 disulfate,
  Ceralution® C: Capric/Caprylic triglyceride, Ceteareth-25, disodium ethylene dicocamide PEG-15 disulfate, Sodium Lauroyl Lactylate, Behenyl Alcohol, Glyceryl Stearate, Glyceryl Stearate Citrate, (INCI names).

The surfactant of formula (I) represents from 3% to 50% of the weight of these mixtures.

The surfactant of formula (I) can be present in the composition according to the invention in a content of active material ranging from 0.05 to 10% by weight, preferably ranging from 0.1 to 5% by weight and better still ranging from 0.2 to 2% by weight, relative to the total weight of the composition.

When it is an emulsion, the aqueous phase of this emulsion may comprise a non-ionic vesicular dispersion prepared according to known processes (Bangham, Standish and Watkins, J. Mol. Biol. 13, 238 (1965), FR 2 315 991 and FR 2 416 008).

The compositions according to the invention find their application in a large number of treatments, especially cosmetic treatments, for the skin, the lips and the hair, including the scalp, especially for protecting and/or caring for the skin, the lips and/or the hair, and/or for making up the skin and/or the lips.

Another subject of the present invention consists of the use of the compositions according to the invention as defined above in the manufacture of products for the cosmetic treatment of the skin, lips, nails, hair, eyelashes, eyebrows and/or scalp, in particular care products, antisun products and makeup products.

The cosmetic compositions according to the invention can be used, for example, as makeup products.

Another subject of the present invention consists of a non-therapeutic cosmetic process for caring for and/or making up a keratin material, which consists in applying, to the surface of said keratin material, at least one composition according to the invention as defined above.

The cosmetic compositions according to the invention may be used, for example, as care products and/or antisun products for the face and/or body with a liquid to semi-liquid consistency, such as milks, more or less smooth creams, cream gels or pastes. They may optionally be packaged in aerosol form and may be in the form of a mousse or a spray.

The compositions according to the invention in the form of vaporizable fluid lotions in accordance with the invention are applied to the skin or the hair in the form of fine particles by means of pressurization devices. The devices in accordance with the invention are well known to those skilled in the art and comprise non-aerosol pumps or "atomizers", aerosol containers comprising a propellant and aerosol pumps using compressed air as propellant. These devices are described in patents U.S. Pat. No. 4,077,441 and U.S. Pat. No. 4,850,517.

The compositions packaged in aerosol form in accordance with the invention generally contain conventional propellants, for instance hydrofluoro compounds, dichlorodifluoromethane, difluoroethane, dimethyl ether, isobutane, n-butane, propane or trichlorofluoromethane. They are preferably present in amounts ranging from 15% to 70% by weight relative to the total weight of the composition.

Assembly

According to another aspect, the invention also relates to a cosmetic assembly comprising:

i) a container delimiting one or more compartment(s), said container being closed by a closing member and optionally being unsealed; and ii) a makeup and/or care composition in accordance with the invention placed inside said compartment(s).

The container may be, for example, in the form of a jar or a box.

The closing member can be in the form of a lid comprising a cap mounted so as to be able to move by translation or by pivoting relative to the container housing said makeup and/or care composition(s).

The examples which follow serve to illustrate the invention without, however, exhibiting a limiting nature. In these examples, the amounts of the composition ingredients are given as weight percentages relative to the total weight of the composition.

EXAMPLES

Preparation Example A

A solution of aqueous ammonia was added dropwise to an ethanolic solution containing 2% by weight of monomethyltriethoxysilane, with stirring, for 3 hours, so as to obtain spherical silica particles with a diameter of 0.8 µm. An isopropanolic solution containing 3% by weight of titanium isopropoxide was provided, with stirring, under a nitrogenous atmosphere, and the resulting particles were filtered off and rinsed, heated in an oven at 300° C. for 4 hours and left to cool to ambient temperature. A hydrated solution of isopropanol containing 5% of titanium hydrolysate was brought into contact with the silica particles in such a way that said hydrolysate adheres to their surface. The particles thus coated were filtered off, rinsed, then heated in an often at 300° C. for 4 hours. The resulting powder was brought into contact with an ethanolic solution containing 10% of tetraethoxysilane. A 1 N hydrochloric acid solution was added dropwise, with stirring, for 24 hours so as to form a layer of silica on the surface of the particles. The powder obtained could then be calcined at 800° C. so as to obtain the multilayer spherical particles. At each coating step, the peak intensity corresponding to the content of titanium dioxide was then measured by X-ray diffraction. The silica (core)/titanium dioxide (first layer)/silica (second layer) content as % weight was 85/5/10 and the diameter of the particles obtained after calcination was 0.6 µm.

Compositions 1 to 4 below were prepared:

| Phase | Ingredients | Ex 1 | Ex 2 | Ex 3 | Ex 4 (outside the invention) |
|---|---|---|---|---|---|
| A1 | Water | 15 | 15 | 15 | 15 |
| | Glycerol | 4 | 4 | 4 | 4 |
| | STYRENE/ACRYLATES COPOLYMER (Sunspheres Powder ®) | 2 | 2 | 2 | 2 |
| A2 | Caprylyl glycol | 0.3 | 0.3 | 0.3 | 0.3 |
| | Glycol | 4 | 4 | 4 | 4 |
| | EDTA | 0.1 | 0.1 | 0.1 | 0.1 |
| B1 | Ceralution H ® | 3 | 3 | 3 | 3 |
| | Alcohol | 0.75 | 0.75 | 0.75 | 0.75 |
| | Isononyl isononanoate | 2 | 2 | 2 | 2 |
| | C12-15 alkyl benzoate (Finsolv TN ®) | 4 | 4 | 4 | 4 |
| | Poly(stearyl acrylate) (Intelimer IPA 13-1 ®) | 1 | 1 | 1 | 1 |
| | Diisopropyl sebacate | 4 | 4 | 4 | 4 |
| | Octocrylene | 3.5 | 3.5 | 3.5 | 3.5 |
| | Avobenzone | 3 | 3 | 3 | 3 |
| | Ethylhexyl Triazone (Uvinul T150 ®) | 2.3 | 2.3 | 2.3 | 2.3 |
| | Drometrizole Trisiloxane (Mexoryl XL ®) | 0.5 | 0.5 | 0.5 | 0.5 |
| B2 | Cyclohexasiloxane (Silsoft 1217 ®) | 2 | 2 | 2 | 2 |
| B3 | Vitamin E | 0.1 | 0.1 | 0.1 | 0.1 |
| C | Water | qs 100 | qs 100 | qs 100 | qs 100 |
| D | Hostacerin AMPS ® | 0.5 | 0.5 | 0.5 | 0.5 |
| E | Crosslinked methacrylic acid/ethyl acrylate copolymer (Carbopol Aqua SF1 ®) | 2 | 2 | 2 | 2 |
| F | Triethanolamine | 0.4 | 0.4 | 0.4 | 0.4 |
| G | Multilayer spherical composite particles $SiO_2/TiO_2/SiO_2$ 82/5/13% by weight with average diameter of 0.6 μm (STM ACS 005050510 ®) | 1.5 | 10 | 25 | 28 |
| H | Terephthalylidenedicamphorsulfonic acid (Mexoryl SX ®) | 1.5 | 1.5 | 1.5 | 1.5 |
| | Triethanolamine | 0.26 | 0.26 | 0.26 | 0.26 |
| I | Alcohol | 7 | 7 | 7 | 7 |

Compositions 1 and 5 below were prepared:

| Phase | Ingredients | Ex 1 | Ex 5 outside the invention |
|---|---|---|---|
| A1 | Water | 15 | 15 |
| | Glycerol | 4 | 4 |
| | STYRENE/ACRYLATES COPOLYMER (Sunspheres Powder ®) | 2 | 2 |
| A2 | Caprylyl glycol | 0.3 | 0.3 |
| | Glycol | 4 | 4 |
| | EDTA | 0.1 | 0.1 |
| B1 | Ceralution H ® | 3 | 3 |
| | Alcohol | 0.75 | 0.75 |
| | Isononyl isononanoate | 2 | 2 |
| | C12-15 alkyl benzoate (Finsolv TN ®) | 4 | 4 |
| | Poly(stearyl acrylate) (Intelimer IPA 13-1 ®) | 1 | 1 |
| | Diisopropyl sebacate | 4 | 4 |
| | Octocrylene | 3.5 | 3.5 |
| | Avobenzone | 3 | 3 |
| | Ethylhexyl Triazone (Uvinul T150 ®) | 2.3 | 2.3 |
| | Drometrizole Trisiloxane (Mexoryl XL ®) | 0.5 | 0.5 |
| B2 | Cyclohexasiloxane (Silsoft 1217 ®) | 2 | 2 |
| B3 | Vitamin E | 0.1 | 0.1 |
| C | Water | qs 100 | qs 100 |
| D | Hostacerin AMPS ® | 0.5 | 0.5 |
| E | Crosslinked methacrylic acid/ethyl acrylate copolymer (Carbopol Aqua SF1 ®) | 2 | 2 |
| F | Triethanolamine | 0.4 | 0.4 |
| G | Multilayer spherical composite particles $SiO_2/TiO_2/SiO_2$ 82/5/13% by weight with average diameter of 0.6 μm (STM ACS 005050510 ®) | 1.5 | 1.5 |
| | Platelet-shaped composite particles of $TiO_2$/Talc (TTC-30 ®) | — | 1.5 |
| H | Terephthalylidenedicamphorsulfonic acid (Mexoryl SX ®) | 1.5 | 1.5 |
| | Triethanolamine | 0.26 | 0.26 |
| I | Alcohol | 7 | 7 |

Emulsion Preparation Method:

The aqueous phase A and oily phase B1 are prepared by mixing the raw materials, with mechanical stirring, at 80° C.; the solutions obtained are macroscopically homogeneous. The emulsion is prepared by slow introduction of the oily phase into the aqueous phase with stirring using a Moritz homogenizer at a stirring speed of 4000 rpm for 15 minutes. The emulsion obtained is cooled, with stirring, to 40° C., then the oily phase B2 and B3 is added thereto with gentle stirring, followed by the phase C. The emulsion obtained is cooled to ambient temperature, then the remaining phases are added thereto with slow stirring. It is characterized by drops less than 10 μm in size.

Protocol for Evaluating In Vitro the Screening Efficiency

The sun protection factor (SPF) is determined according to the "in vitro" method described by B. L. Diffey in J. Soc. Cosmet. Chem. 40, 127-133, (1989). The measurements were made using a UV-1000S spectrophotometer from the company Labsphere. Each composition is applied to a rough plate of PMMA, in the form of a uniform and even deposit in a proportion of 1 mg/cm².

Protocol for Evaluating the Stability of the Compositions of the Invention

The stability of the compositions of the invention is evaluated by macroscopic and microscopic observations of their appearance. A composition is judged to be stable (+) when these appearances do not vary over time. A composition is judged to be unstable (−) when at least one of these appearances varies. The examples illustrate this stability of a period of 9 months at ambient temperature.

Protocol for Evaluating the Glide after Application to the Skin

The glide after application of the formula to the skin is evaluated by applying the formula to a forearm in a proportion of 2 mg/cm², waiting for a drying time equal to 2 minutes and then assessing the friction force felt between the fingers and the surface of the forearm. The results are given in the table below:

| Measurements | Ex 1 | Ex 2 | Ex 3 | EX 4 outside the invention |
|---|---|---|---|---|
| Stability | + | + | + | −<br>Release of oil observable by eye at 9 months |

|  |  |  |  |  |
|---|---|---|---|---|
| In vitro SPF | 88.8 ± 8.2 | 104.1 ± 18.5 | 142.2 ± 13 | 197.4 ± 11.4 |
| Glide (non-greasy) | + | + | + | − |

| Measurements | Ex 1 | Ex 5 outside the invention |
|---|---|---|
| Stability | + | + |
| In vitro SPF | 88.8 ± 8.22 | 92.5 ± 5.9 |

Compositions 1 to 3 of the invention comprising less than 28.0% by weight of multilayer spherical composite particles (STM ACS 005050510®) have a better stability and better sensory properties than composition 4 outside the invention comprising 28.0% by weight of multilayer spherical composite particles (STM ACS 005050510®).

Composition 1 of the invention comprising the multilayer spherical composite particles according to the invention (STM ACS 005050510®) alone exhibits an effectiveness and a stability that are equivalent to those of composition 5 (outside the invention according to WO 2012/104161) comprising multilayer spherical particles according to the invention (STM ACS 005050510®) combined with TTC 30® platelet-shaped composite particles.

The invention claimed is:

1. A composition comprising:
   a) at least multilayer spherical composite particles comprising
      i) a core comprising at least one material A having a refractive index ranging from 1.3 to 1.8; and
      ii) at least one layer covering said core, comprising at least one material B having a refractive index ranging from 1.9 to 3.1; and
      iii) optionally at least one second layer covering the material B, comprising at least one material C having a refractive index ranging from 1.3 to 1.8;
   said composite particles being present in an amount less than 28.0% by weight relative to the total weight of the composition; and
   b) at least one UV-screening agent.

2. The composition according to claim 1 in which the multilayer spherical composite particles comprise:
   i) a core comprising at least one material A having a refractive index ranging from 1.3 to 1.8;
   ii) at least one layer covering said core, comprising at least one material B having a refractive index ranging from 1.9 to 3.1; and
   iii) at least one second layer covering the material B, comprising at least one material C having a refractive index ranging from 1.3 to 1.8.

3. The composition according to claim 1, in which the multilayer spherical composite particles are characterized by an average diameter of between 0.05 and 45 μm.

4. The composition according to claim 1, in which the multilayer spherical composite particles are present at concentrations ranging from 1% to 25% by weight relative to the total weight of the composition.

5. The composition according to claim 1, in which the materials A, B and C are organic or inorganic.

6. The composition according to claim 1, in which
   the organic materials A and C are selected from the group consisting of poly(meth)acrylates, polyamides, silicones, polyurethanes, polyethylenes, polypropylenes, polystyrenes, polycaprolactams, polysaccharides, polypeptides, polyvinyl derivatives, waxes, polyesters and polyethers, and mixtures thereof;
   the inorganic materials A and C are selected from the group consisting of glass, silica, calcium carbonate and aluminium oxide, and mixtures thereof;
   the inorganic material B is chosen from metal oxides.

7. The composition according to claim 1, in which
   the materials A and C are silica;
   the material B is titanium dioxide ($TiO_2$).

8. The composition according to claim 1, in which the multilayer spherical composite particles comprise:
   i) a core consisting of silica and
   ii) at least one layer consisting of titanium dioxide covering said core and
   iii) at least one second layer consisting of silica covering said titanium dioxide layer.

9. The composition according to claim 1, in which
   the core based on the material A represents from 1% to 99% by weight relative to the total weight of the spherical composite particle;
   the layer based on the material B represents from 0.5% to 50% by weight relative to the total weight of the spherical composite particle;
   the layer based on the material C represents from 0.5% to 50% by weight relative to the total weight of the spherical composite particle.

10. The composition according to claim 1, in which the UV-screening agent is in free form.

11. The composition according to claim 1, in which the organic UV-screening agent(s) is (are) selected from the group consisting of cinnamic compounds; anthranilate compounds; salicylic compounds; dibenzoylmethane compounds; benzylidenecamphor compounds; benzophenone compounds; β,β-diphenylacrylate compounds; triazine compounds; benzotriazole compounds; benzalmalonate compounds; benzimidazole compounds; imidazoline compounds; bis-benzazolyl compounds; p-aminobenzoic (PABA) compounds; methylenebis(hydroxyphenylbenzotriazole) compounds; benzoxazole compounds; screening polymers and screening silicones; α-alkylstyrene-based dimers; 4,4-diarylbutadiene compounds; merocyanines, and mixtures thereof.

12. The composition according to claim 11, in which the organic screening agent(s) is (are) selected from the group consisting of
   Ethylhexyl methoxycinnamate,
   Ethylhexyl salicylate,
   Homosalate,
   Butyl methoxy dibenzoylmethane,
   Octocrylene,
   Phenylbenzimidazolesulfonic acid,
   n-Hexyl 2-(4-diethylamino-2-hydroxybenzoyl)benzoate,
   Terephthalylidenedicamphorsulfonic acid,
   Methylenebis(benzotriazolyl)tetramethylbutylphenol,
   2,4,6-tris(diphenyl)triazine,
   Bis(ethylhexyloxyphenol)methoxyphenyltriazine,
   Ethylhexyl triazone,
   Diethylhexyl butamido triazone,
   Drometrizole trisiloxane,
   and mixtures thereof.

13. The composition according to claim 1, in which the UV-screening agent is selected from the group consisting of inorganic UV-screening agents, and more preferentially coated or uncoated metal oxides having an average elementary particle size of less than or equal to 0.5 μm.

14. The composition according to claim 1, comprising, in addition, at least one crosslinked copolymer of methacrylic acid and of $C_1$-$C_4$ alkyl acrylate.

15. The composition according to claim 1, comprising, in addition, at least one semi-crystalline polymer which is solid at ambient temperature and which has a melting point greater than or equal to 30° C., comprising a) a polymer backbone and b) at least one crystallizable organic side chain and/or one crystallizable organic block which is part of the backbone of said polymer, said polymer having a number-average molecular weight Mn greater than or equal to 1000.

16. The composition according to claim 1, comprising, in addition, hollow latex particles having a particle size ranging from 150 to 380 nm.

17. The composition according to claim 1, comprising, in addition, at least one surfactant of formula (I) below:

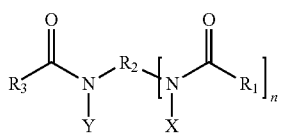

in which:
$R_1$ and $R_3$ denote, independently of each other, an alkyl radical containing from 1 to 25 carbon atoms;
$R_2$ denotes a spacer group consisting of a linear or branched alkylene chain containing from 1 to 12 carbon atoms;
X denotes a —$(C_2H_4O)_a$—$(C_3H_6O)_b$Z group
Y denotes a —$(C_2H_4O)c$-$(C_3H_6O)_d$Z group
where:
Z denotes a hydrogen atom or a —$CH_2$—COOM, —$SO_3$M, —P(O)(OM)$_2$,
$C_2H_4$—$SO_3$M, —$C_3H_6$—$SO_3$M or —$CH_2(CHOH)_4$CH$_2$OH radical, where M, M' represent H or an alkali metal ion or alkaline-earth metal ion or ammonium ion or alkanolammonium ion,
a and c, independently of one another, range from 0 to 15,
b and d, independently of one another, range from 0 to 10, and
the sum of a+b+c+d ranges from 1 to 25; and
n ranges from 1 to 10, and more particularly the compound disodium ethylene dicocamide PEG-15 disulfate, having the following structure:

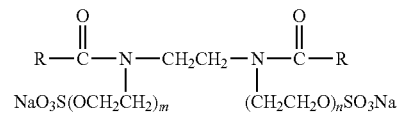

where RCO represents a coconut fatty acid radical and m+n has an average value of 15.

* * * * *